(12) United States Patent
Mukumoto

(10) Patent No.: US 8,349,621 B2
(45) Date of Patent: Jan. 8, 2013

(54) LIGAND MOLECULE-IMMOBILIZED POLYMER, LIGAND MOLECULE-IMMOBILIZED PARTICLE, METHOD OF DETECTING TARGET SUBSTANCE, AND METHOD OF SEPARATING TARGET SUBSTANCE

(75) Inventor: Kousuke Mukumoto, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 245 days.

(21) Appl. No.: 12/276,964

(22) Filed: Nov. 24, 2008

(65) Prior Publication Data

US 2009/0137064 A1    May 28, 2009

(30) Foreign Application Priority Data

Nov. 28, 2007  (JP) ................................. 2007-307486
May 8, 2008    (JP) ................................. 2008-122163

(51) Int. Cl.
   *G01N 33/549*    (2006.01)

(52) U.S. Cl. ........ 436/532; 436/501; 436/518; 436/528; 436/531; 525/54.1; 525/165; 525/167; 525/329.7; 525/329.9; 525/330.2; 525/330.3; 525/333.6; 525/360; 525/366; 525/327.6; 525/327.8

(58) Field of Classification Search ................. 436/501, 436/518, 528, 531, 532; 525/54.1, 165, 167, 525/329.7, 329.9, 330.2, 330.3, 333.6, 360, 525/366, 32, 7.6, 327.8
See application file for complete search history.

(56) References Cited

U.S. PATENT DOCUMENTS

2002/0160472 A1   10/2002  Handa et al.
2005/0136258 A1*   6/2005  Nie et al. ...................... 428/402

FOREIGN PATENT DOCUMENTS

JP    S59-135887 A    8/1984
JP     3086427 B2     9/2000

OTHER PUBLICATIONS

Caruso, Adv. Mater. 2001, 13, No. 1, p. 11-22.*

* cited by examiner

*Primary Examiner* — Robert C Boyle
(74) *Attorney, Agent, or Firm* — Canon U.S.A., Inc., IP Division

(57) ABSTRACT

A ligand molecule-immobilized polymer has a structure represented by the following general formula (1).

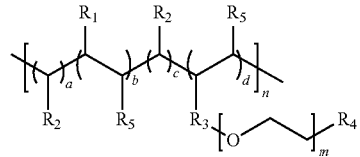

In the general formula (1), $R_1$ represents a ligand molecule-containing group, $R_2$ represents a hydrophobic group, $R_3$ represents a spacer site, $R_4$ represents a hydrophilic group, $R_5$ represents a group having charge, a to d specify a composition ratio and each represent an integer of 1 or more, and n and m specify chain lengths and represent integers satisfying the relationships of $1 \leq n(a+b+c+d) \leq 10{,}000$ and $1 \leq m \leq 350$.

4 Claims, 7 Drawing Sheets

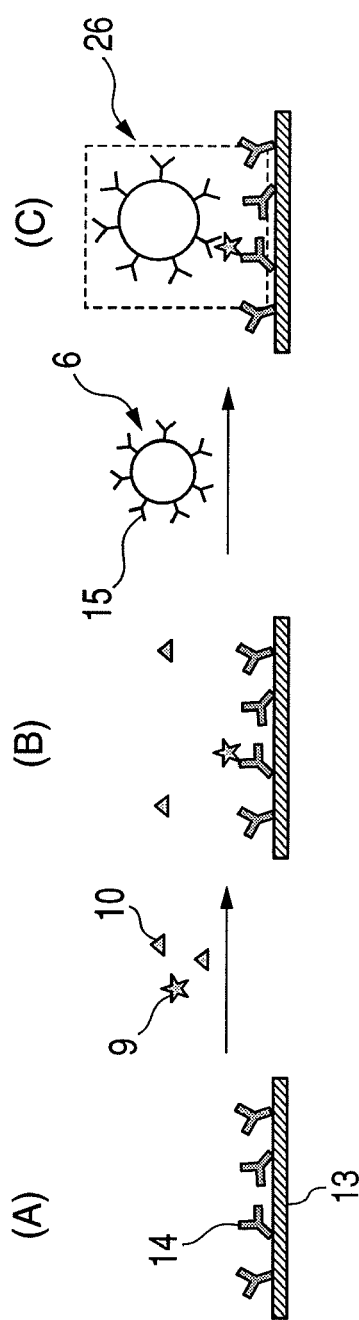
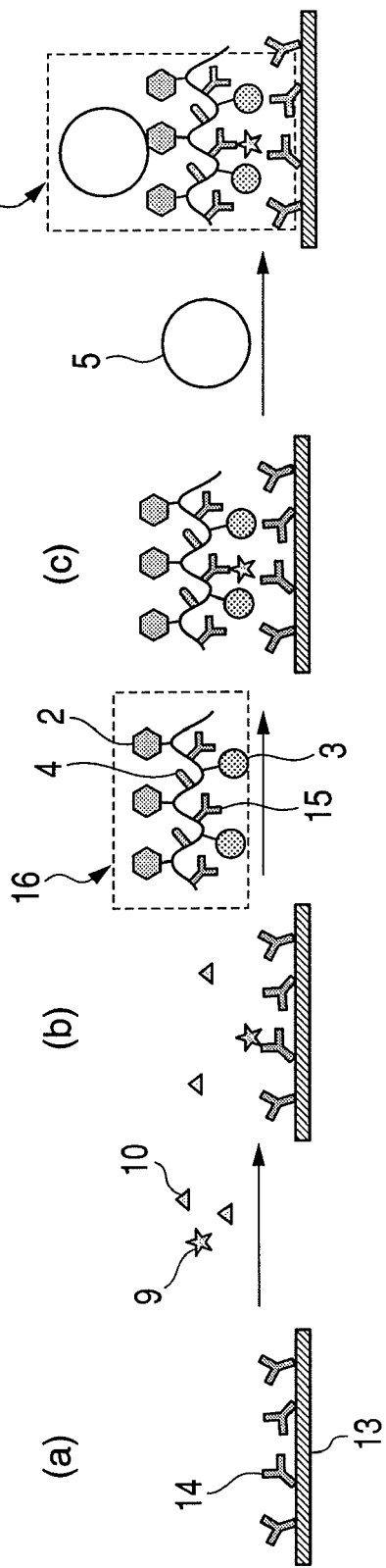

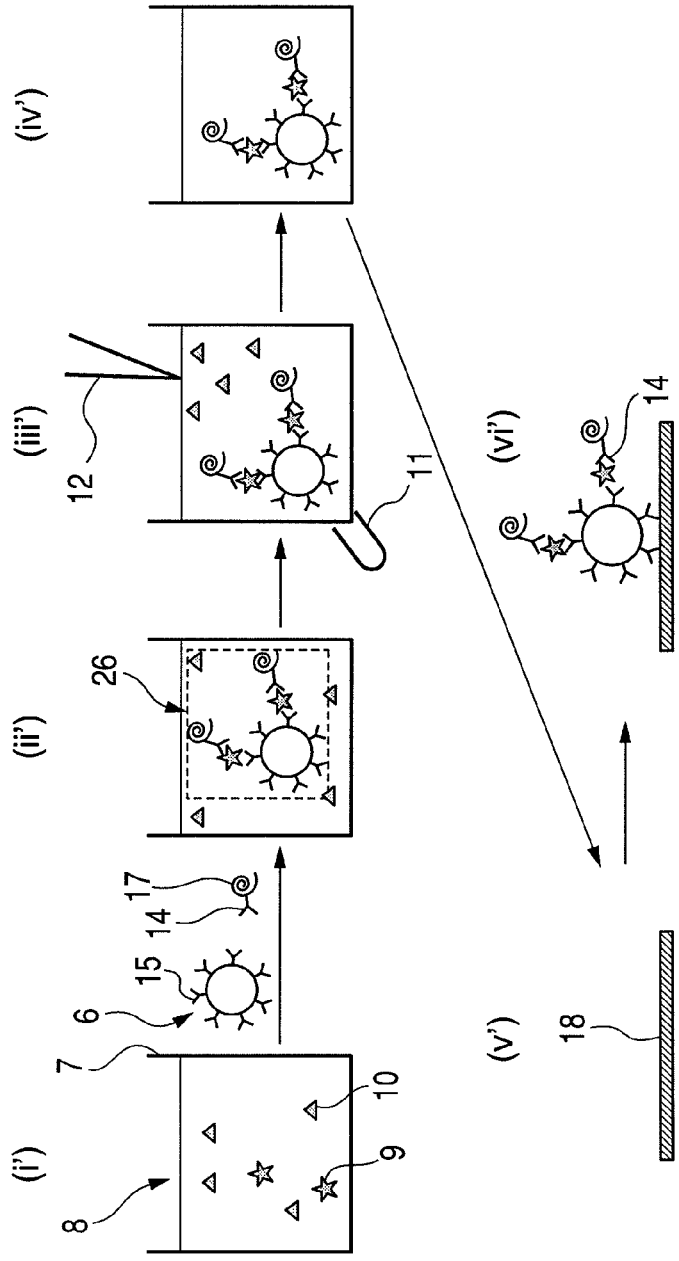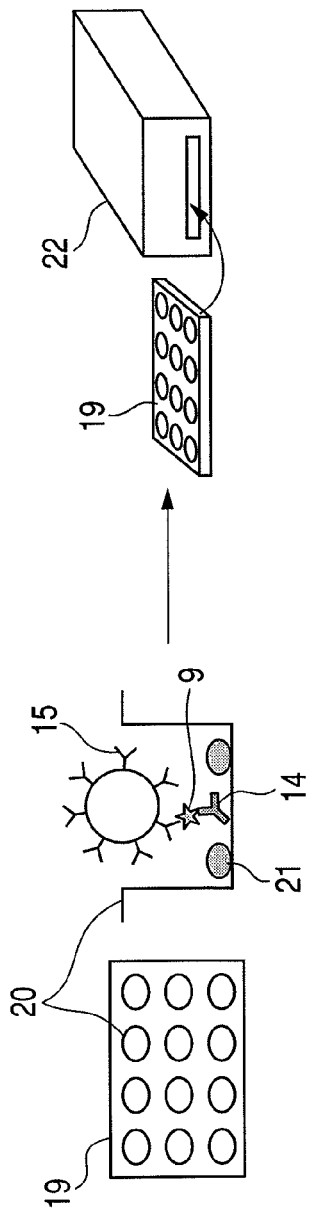
FIG. 5
FIG. 6

LIGAND MOLECULE-IMMOBILIZED POLYMER, LIGAND MOLECULE-IMMOBILIZED PARTICLE, METHOD OF DETECTING TARGET SUBSTANCE, AND METHOD OF SEPARATING TARGET SUBSTANCE

BACKGROUND OF THE INVENTION

1. Field of the Invention

The present invention generally relates to a ligand molecule-immobilized polymer, a ligand molecule-immobilized particle, a method of detecting a target substance, and a method of separating a target substance.

2. Description of the Related Art

Particles to which biological molecules such as ligand molecules are immobilized have been widely used as affinity purification reagents or sample test reagents in recent years. These particles are typically excellent in dispersibility and show a high affinity for a target substance, and thus a method of producing such particles having these properties has been sought. In other words, there has been a need for a method of producing particles to which ligand molecules are immobilized having the following characteristics: in the production of the particles, the aggregation of the particles does not excessively occur at the time of the immobilization of the ligand molecules to the particles, and a large amount of the ligand molecules can be efficiently immobilized.

Japanese Patent Application Laid-Open No. S59-135887 discloses a method involving: covering the surfaces of hydrophobic particles with a hydrophilic polymer having a functional group; and immobilizing a ligand molecule to the functional group of the hydrophilic polymer. In the method, the ligand molecule is strongly immobilized to each particle through the functional group by a covalent bond, and, furthermore, the surface of each particle is covered with a hydrophilic group, and hence the aggregation of the particles at the time of the immobilization of the ligand molecule is reduced, and ligand molecule-immobilized particles may be produced in good yield.

In addition, Japanese Patent No. 3086427 discloses a method involving: covering the surfaces of hydrophobic particles with a glycidyl methacrylate polymer; and immobilizing a physiologically active substance to a functional group present on the surface of each particle through a chemical bond. The method allows the production of particles having excellent dispersibility and physiological activity because the surface of each particle is covered with a hydrophilic polymer.

However, neither of the methods described in Japanese Patent Application Laid-Open No. S59-135887 and Japanese Patent No. 3086427 allows the immobilization of a sufficiently large amount of ligand molecules to the surfaces of particles, because the number of functional groups that can be formed on the surfaces of the particles is limited. As a result, the affinity of each particle for a target substance is reduced. In addition, since the immobilization reaction is a heterogeneous chemical reaction, the efficiency with which the ligand molecules are immobilized may be poor, and thus a large amount of ligand molecules may be needed for the reaction.

SUMMARY OF THE INVENTION

According to one embodiment of the present invention, there is provided a ligand molecule-immobilized polymer characterized by having a structure represented by the following general formula (1):

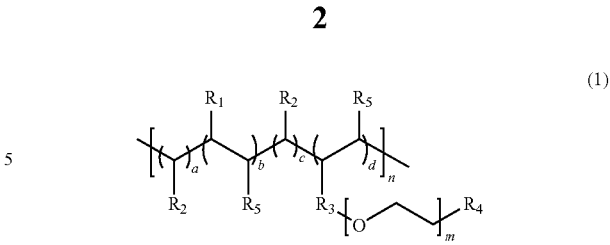

where $R_1$ represents a ligand molecule-containing group, $R_2$ represents a hydrophobic group, $R_3$ represents a spacer site, $R_4$ represents a hydrophilic group, $R_5$ represents a group having charge, a to d specify a composition ratio and each represent an integer of 1 or more, and n and m specify chain lengths and represent integers satisfying relationships of $1 \leq n(a+b+c+d) \leq 10{,}000$ and $1 \leq m \leq 350$.

According to another embodiment of the present invention, there is provided a ligand molecule-immobilized particle including: a core particle, a surface of which has hydrophobicity and charge; and a ligand molecule-immobilized polymer immobilized to the surface of the core particle, in which: the ligand molecule-immobilized polymer is the above-described ligand molecule-immobilized polymer; and a charge $Q_1$ of the group having charge in the ligand molecule-immobilized polymer, and a charge $Q_2$ on the surface of the core particle satisfy a relationship of $Q_1 \times Q_2 < 0$ in a sample liquid.

According to yet another embodiment of the present invention, there is provided a method of separating a target substance including: (1) forming a composite A of the ligand molecule of the above-described ligand molecule-immobilized particle, and the target substance captured by the ligand; and (2) separating the composite A.

According to a further embodiment of the present invention, there is provided a method of detecting a target substance including: (I) forming a composite B formed of a first ligand that is immobilized to a support, and the target substance captured by the first ligand; and (II) forming a composite C of a second ligand that is the ligand molecule of the above-described ligand molecule-immobilized particle, and the composite B, wherein the target substance is also captured by the second ligand; and (III) detecting the target substance in the composite C.

Further features of the present invention will become apparent from the following description of exemplary embodiments with reference to the attached drawings.

BRIEF DESCRIPTION OF THE DRAWINGS

FIG. 3 illustrates schematic views (A), (B) and (C) for describing an embodiment of a method of detecting a target substance involving the use of the ligand molecule-immobilized particle as a labeling agent.

FIG. 4 illustrates schematic views (a), (b), (c) and (d) for describing an embodiment of a method of detecting the target substance involving combining a ligand molecule-immobilized polymer and a particle.

FIG. 5 illustrates schematic views (i'), (ii'), (iii'), (iv'), (v') and (vi') for describing an embodiment of a method of detecting the target substance involving the use of the ligand molecule-immobilized particle as a carrier.

FIG. 6 is a schematic view for describing an embodiment of a sandwich immunoassay using a microwell plate.

DESCRIPTION OF THE EMBODIMENTS

Figure 1:
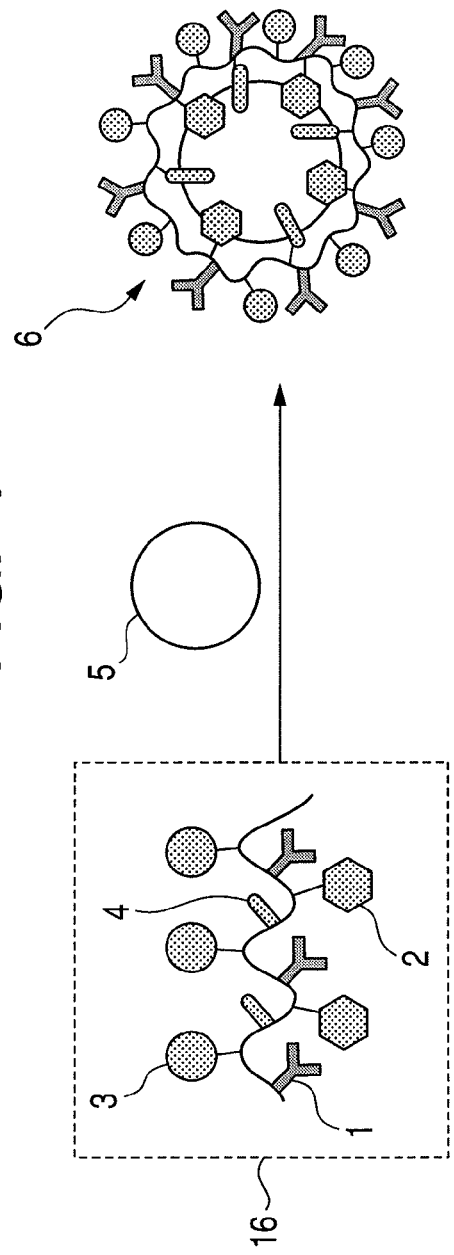
FIG. 1 is a schematic view of a ligand molecule-immobilized particle in the present invention.

Hereinafter, the present invention will be described in greater detail. It should be noted that the present invention is specified by the claims, and thus is not intended to be construed as being limited to the following embodiments and examples. For example, one of ordinary skill in the art can realize the present invention by freely changing, for example, materials, composition conditions, and reaction conditions in the following embodiments and examples.

According to a first embodiment of the present invention, there is provided a ligand molecule-immobilized polymer characterized by having a structure represented by the following general formula (1):

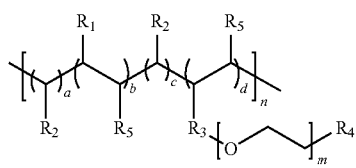

(1)

where $R_1$ represents a ligand molecule-containing group, $R_2$ represents a hydrophobic group, $R_3$ represents a spacer site, $R_4$ represents a hydrophilic group, $R_5$ represents a group having charge, a to d specify a composition ratio and each represent an integer of 1 or more, and n and m specify chain lengths and represent integers satisfying relationships of $1 \leq n(a+b+c+d) \leq 10,000$ and $1 \leq m \leq 350$.

In one version, the quantity n(a+b+c+d), representing or relating to the number of carbon atoms of the main chain backbone of the ligand molecule-immobilized polymer, may range from 1 to 10,000, and the ligand molecule-immobilized polymer may have a molecular weight of from 1,000 to 100,000 kDa.

According to one aspect of the invention, the structure of the ligand molecule-immobilized polymer may not be particularly limited, as long as the structure has four components, i.e., a ligand molecule-containing group ($R_1$), a hydrophobic group ($R_2$), a hydrophilic site ($-[O-CH_2-CH_2]_m-R_4$) (provided that $R_4$ represents a hydrophilic group), and a group having charge ($R_5$), and satisfies the above conditions. Therefore, the ligand molecule-immobilized polymer may be, for example, a polymer obtained by polymerizing a unit having those components as a monomer unit, or as another example, may be a copolymer obtained by copolymerizing two or more different monomer units. In addition, in the case of the copolymer, each monomer unit may contain one of the components, or may contain two or more of the components. Also, the structure of such a copolymer may be any one of a random copolymer, an alternating copolymer, a period copolymer, and a block copolymer. It should be noted that the ligand molecule-immobilized polymer may also optionally comprise a monomer unit that is free of any one of the above functional components.

In one version, when the polymer represented by the general formula (1) is a polymer obtained by copolymerizing two or more monomer units, the polymer may be, for example, a random copolymer represented by the following general formula (2) shown below, which is formed of units having the following characteristics: one unit is formed of a unit in the general formula (1) the number of which is represented by a, and a unit in the general formula (1) the number of which is represented by b, where the number of the units is represented by a+b; and the other unit is formed of a unit in the general formula (1) the number of which is represented by c, and a unit in the general formula (1) the number of which is represented by d, where the number of the other units is represented by c+d.

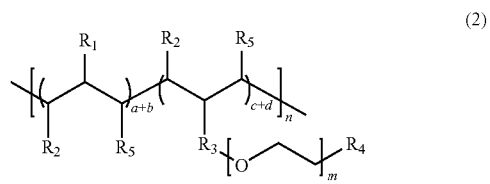

(2)

In formula (2) above, $R_1$ represents a ligand molecule-containing group, $R_2$ represents a hydrophobic group, $R_3$ represents a spacer site, $R_4$ represents a hydrophilic group, $R_5$ represents a group having charge, a+b and c+d specify a composition ratio and each represent an integer of 1 or more, and n and m specify chain lengths and n represents an integer satisfying relationships of $1 \leq n(a+b+c+d) \leq 10,000$ and $1 \leq m \leq 350$.

Alternatively, in another version, the ligand molecule-immobilized polymer can be obtained by: synthesizing a polymer by using a monomer unit free of any one of the components and having a group which can be modified by the addition of any one of the components; and adding the components to the polymer. In yet another version, the ligand molecule-immobilized polymer can be obtained by: polymerizing a monomer unit containing at least one, but not all, of the components and having a group to which any one of the remaining components can be added; and adding the remaining components to the resultant polymer. According to some embodiments of such production methods, an unreacted group may remain in some cases, and hence the polymer represented by the general formula (1) may also contain a unit free of any one of the components.

Hereinafter, each portion of the ligand molecule-immobilized polymer will be described in greater detail.

<Ligand Molecule-Containing Group>

In the embodiment of the ligand molecule-immobilized polymer shown in general formula (1), $R_1$ represents a ligand molecule-containing group, and, more specifically, represents a ligand molecule or a spacer-containing ligand molecule. The term "ligand molecule" refers to a substance capable of specifically recognizing and capturing (e.g., binding to) a target substance. Examples of combinations of the target substance and the ligand molecule may be, for example, a combination of: an antigen and an antibody; a peptide and an antibody; a virus and an antibody; a low-molecular weight compound and an antibody; a cell and an antibody; an antigen and an aptamer; an antigen and an enzyme; a peptide and a protein; a peptide and a peptide; DNA and a protein; RNA and a protein; a sugar and a protein; a protein and a protein; and a sugar and a sugar. It should be noted that the expression "the combination of the target substance and the ligand molecule is A-B" includes both the case where the target substance is A and the ligand molecule is B, and the case where the target substance is B and the ligand molecule is A. In a version where an antigen is used as the target substance and an antibody is used as the ligand molecule, a monoclonal antibody obtained from a clone derived from a single antibody-forming cell, a polyclonal antibody purified from a serum of an animal immunized with an antigen, or the like can be used. It should be noted that antigens are substances that induce antibodies, such as the antibodies above, and can be classified as non-biological molecules or biological molecules. Antigens having a high value for industrial usage that are classified as non-biological molecules may be, for example, PCB's that differ from each other in the number of chlorine substituents, or the substitution positions of the chlorine substituents, and that may act as environmental pollutants, dioxins that differ from each other in the number of chlorine substituents, or the substitution positions of the chlorine substituents, and endocrine disruptors that may also be known as environmental hormones. In addition, examples of antigens classified as biological molecules may contain a biological substance selected from at least one of a nucleic acid, a protein, a sugar chain, lipid, and a composite thereof. To be additionally specific, in one embodiment, the present invention may be applicable to any substance as long as the biological molecule contains a substance selected from at least one of DNA, RNA, an aptamer, a gene, a chromosome, a cell membrane, a virus, an antigen, an antibody, a lectin, a hapten, a hormone, a receptor, an enzyme, a peptide, a sphingo sugar, and a sphingoglycolipid.

In one embodiment according to the invention, the ligand molecule-containing group can be bound to the polymer by utilizing a chemical bond or an affinity bond. Here, the term "chemical bond" refers to a bond formed in association with the exchange of an electron between atoms or ions, and examples of the chemical bond can include a covalent bond, a coordinate bond, and a metallic bond. Methods of binding the group to the polymer involving the utilization of the chemical bond may include, for example, at least one of a method involving immobilizing the group by an amide bond, a method involving immobilizing the group through glutaraldehyde, a method involving immobilizing the group with N-hydroxysuccinimide ester through a spacer by an amide bond, and a method involving immobilizing the group with maleimide through a spacer by a thiol bond. In addition, examples of methods of binding the group to the polymer involving the utilization of the affinity bond may include, for example, at least one of a method involving immobilizing the group by a biotin-avidin bond, a method involving immobilizing the group by Protein A and Protein G, a method involving immobilizing the group by an antigen-antibody reaction, a method involving immobilizing the group by utilizing a sandwich bond as a result of a combination of the bond, proteins, and a reaction, and a method involving immobilizing the group by DNA-DNA or DNA-PNA hybridization.

It should be noted that, in one version in accordance with the invention, the ligand molecule-containing group may be bound under such moderate temperature and chemical conditions that no denaturation occurs, in order that the activity of the ligand molecule is not impaired, such that the ligand molecule may be used in applications for the detection and separation of the target substance. For example, in one version, a method involving synthesizing the main chain of the polymer and adding the ligand molecule after the synthesis can be suitably employed. Such a method may comprise, for example, a method involving introducing the ligand molecule and polyethylene glycol into a styrene-maleic anhydride copolymer having an acid anhydride site showing high activity.

<Hydrophobic Group>

$R_2$ in the embodiment of the ligand molecule-immobilized polymer shown in general formula (1) represents a hydrophobic group. Here, the term "hydrophobic" as used in the present invention and the present specification refers to a property of the group such that an affinity of the group for water is low and polarity is also low. In one version, the hydrophobic group in the ligand molecule-immobilized polymer may have the action of immobilizing the ligand molecule-immobilized polymer to the surface of a core particle by a hydrophobic interaction. Examples of such hydrophobic groups may include, but are not limited to, a substituted or unsubstituted chain saturated hydrocarbon, a substituted or unsubstituted chain unsaturated hydrocarbon, a substituted or unsubstituted alicyclic saturated hydrocarbon, a substituted or unsubstituted alicyclic unsaturated hydrocarbon, a substituted or unsubstituted aromatic hydrocarbon, and a substituted or unsubstituted heteroaromatic hydrocarbon. In one version, the hydrophobic group may comprise a group formed of an aromatic hydrocarbon structure. Additional specific examples of the structure of the hydrophobic group may be a benzene derivative, a naphthalene derivative, an anthracene derivative, or a pyrene derivative. It should be noted that the phrase "substituted A" as used herein includes both the case where a carbon atom of the main chain of A is substituted with any other atom, and the case where a hydrogen atom of a side chain of A is substituted with any other atom. Therefore, in one version, a substituted aromatic hydrocarbon can include one in which hydrogen contained in the aromatic ring is substituted with another functional group. For example, hydrogen atoms in one or more of benzene rings, naphthalene rings, anthracene rings, and pyrene rings of the aromatic hydrocarbons may be substituted with at least one of primary to quaternary amino groups, carboxyl groups, hydroxy groups, nitro groups, sulfonyl groups, alkyl groups having 1 to 10 carbon atoms, isopropyl groups, acyl groups, and halogen elements. It should be noted that such functional groups may chemically bind to, or otherwise interact with, a particle. As an example, in a version where a thiol group is used as a group that binds to a particle by utilizing a chemical bond, the polymer can be bound to a particle having gold on its surface by a gold-thiol bond. As another example, in a version where an azide group is used as the group, the polymer can be bound to the surface of a particle, the surface being aminated, by a photo-crosslinking reaction. In one version, a functional group that binds to a particle by utilizing an interaction may be, for example, an acidic group (acidic functional group) or a basic group (basic functional group). When the acidic group or the basic group is used, the ligand molecule-immobilized polymer may electrostatically interact with a charge that the core particle has on its surface, so as to become immobilized to the core particle. It should be noted that, in one version, the acidic group described herein may be a group that readily becomes negatively charged in a liquid, and examples of such groups may include at least one of a carboxyl group, a sulfonyl group, a nitro group, a phosphate group, and a hydroxyl group. On the other hand, in one version, the basic group described herein may be a group that readily becomes positively charged in a liquid, and examples of such groups may include at least one of primary to quaternary amines. Accordingly, in one embodiment, when the aromatic hydrocarbon is a benzene derivative, a naphthalene derivative, an anthracene derivative, or a pyrene derivative, the hydrophobic group can contain any such aromatic ring a hydrogen atom of which is substituted with any one of the groups listed above, and, furthermore, may contain any such aromatic ring a hydrogen atom of which is substituted with a lower alkyl or alkoxy group having 1 to 6 carbon atoms.

<Hydrophilic Site>

In the embodiment of the ligand molecule-immobilized polymer shown in general formula (1), the portion $-[O-CH_2-CH_2-]_m-R_4$ in the ligand molecule-immobilized polymer is a hydrophilic site. Here, the term "hydrophilic site" as used in the present invention refers to a site showing a high affinity for water and having high polarity. In addition, $R_4$ in this embodiment represents a hydrophilic group serving as a terminal group (terminal functional group) bound to $-[O-CH_2-CH_2]_m$. In one version, the hydrophilic site including $R_4$ functions as an agent for preventing the aggregation of particles, or as an agent for preventing the non-specific adsorption of a contaminant to the surface of each particle. Examples of the hydrophilic group $R_4$ may include, but are not limited to, hydrogen, a carboxyl group, a sulfo group, a phosphate group, primary to quaternary amino groups, a hydroxy group, and phosphorylcholine derivatives. Note that, in one version, $-[O-CH_2-CH_2-]_m-R_4$ may represent any one of monoethylene glycol, oligoethylene glycol, and polyethylene glycol, and m may represent 1 or more to 350 or less. For example, an oligoethylene glycol in which m represents 10 or more and 350 or less, or a polyethylene glycol in which m represents 10 or more and 350 or less, may be used.

$R_3$ in the ligand molecule-immobilizing polymer represents a spacer site that connects the hydrophilic site represented by $-[O-CH_2-CH_2-]_m-R_4$ in the ligand molecule-immobilized polymer and the ligand molecule-immobilized polymer main chain. For example, the spacer site can comprise one or more of a substituted or unsubstituted hydrocarbon group, a substituted or unsubstituted amide group, a substituted or unsubstituted imine group, a substituted or unsubstituted urea group, a substituted or unsubstituted thiourea group, a substituted or unsubstituted sulfone amide group, a substituted or unsubstituted aziridine group, a substituted or unsubstituted triazole group, a substituted or unsubstituted ester group, a substituted or unsubstituted ether group, a substituted or unsubstituted thioether group, and the like. In one version, the spacer site may be formed of a substituted or unsubstituted hydrocarbon group, such as a hydrocarbon group formed of a linear or branched alkyl group having 20 or less carbon atoms, or even a hydrocarbon group having 12 or less carbon atoms out of those groups.

<Group Having Charge>

In the embodiment of the ligand molecule-immobilized polymer shown in general formula (1), $R_5$ represents a group having charge. In this embodiment, the group having charge has charge in a liquid, such as at least in a liquid being used as a sample, and may also have an action of immobilizing the ligand molecule-immobilized polymer onto the surface of the core particle by an electrostatic interaction. Examples of such groups having charge $R_5$ may be a group having cationic or anionic properties, and additionally specific examples of such a group can include an acidic group and a basic group. The acidic group described herein may be a group that readily becomes negatively charged in a liquid, and examples of such a group may include, but are not limited to, a carboxyl group, a sulfonyl group, a nitro group, a phosphate group, and a hydroxyl group. On the other hand, the basic group described herein may be a group that readily becomes positively charged in a liquid, and examples of such a group may include, but are not limited to, primary to quaternary amines. It should be noted that the sample liquid described herein refers to a solution that may be used as a measuring object containing the target substance, and examples of the sample liquid can include, but are not limited to, blood, a lymph fluid, a tissue fluid, a spinal fluid, urea, a coelomic fluid, a dialyzing fluid, and an aqueous solution, each of which contains the target substance.

Next, a second embodiment of the present invention will be described.

According to the second embodiment of the present invention, there is provided a ligand molecule-immobilized particle characterized by being formed of: a core particle; and the above-mentioned ligand molecule-immobilized polymer that is immobilized to a surface of the core particle.

FIG. 1 shows an example of the ligand molecule-immobilized particle according to the second embodiment of the present invention.

In the embodiment shown in FIG. 1, a ligand molecule-immobilized particle 6 is formed of a core particle 5 and a ligand molecule-immobilized polymer 16 according to the first embodiment of the present invention that is immobilized to the surface of the particle. In one version, the ligand molecule-immobilized polymer 16 may be immobilized to the core particle 5 through both hydrophobic interactions and electrostatic interactions at multiple points.

In one embodiment, the surface of the core particle 5 has both hydrophobicity and charge. For example, in one version, as long as the core particle 5 has the above properties, the entirety of the particle may be formed of a single material having hydrophobicity and charge, or the particle may be formed of multiple layers, the outermost layer out of which is formed of a material having hydrophobicity and charge. In the latter case, any layer except the outermost layer may be formed of a material that is other than the material having hydrophobicity and charge. Alternatively, in another version, the surface of the core particle may have a region formed of a material having charge and another region formed of a material having hydrophobicity. It should be noted that the term "hydrophobicity" as used in the present invention refers to a property such that the material has little or no solubility in water but is at least partially, and even entirely, soluble in oil.

It should be noted that the expression "the surface of the core particle 5 has charge" means that at least the surface of the core particle 5 has charge when placed in a sample liquid. In one version, a charge $Q_1$ of the group having charge in the ligand molecule-immobilized polymer 16, and a charge $Q_2$ on the surface of the core particle, satisfy a relationship of $Q_1 \times Q_2 < 0$, in the sample liquid.

Therefore, in one embodiment, hydrophobic groups 2 and groups 4 that each have charge in the ligand molecule-immobilized polymer 16 may be positioned on the side of the particle in relation to the main chain of the polymer, and hydrophilic groups 3 and ligand molecules 1 in the polymer may be positioned on the side opposite to the particle in relation to the main chain.

As a result, in one embodiment, a hydrophobic interaction may arise between each hydrophobic group $R_2$ of the ligand molecule-immobilized polymer 16 and the surface of the core particle 5, and an electrostatic interaction may arise between each group $R_5$ having charge of the ligand molecule-immobilized polymer and the surface of the core particle, whereby the ligand molecule-immobilized polymer may be strongly immobilized to the core particle.

Examples of the material that may be suitable when the core particles each are formed of a material having hydrophobicity and charge may include a hydrophobic polymer having charge containing at least one of a carboxyl group, a sulfonyl group, primary to quaternary amino groups, and the like. More specific examples may include, but are not limited to, poly(4-styrene carboxylic acid), poly(4-aminostyrene), poly (4-styrenesulfonic acid), polyacrylic acid derivatives, polymethacrylic acid derivatives, polyamine, polyimide, and polyamic acid. In addition, in one version, the material may have an aliphatic acid containing an alkyl group having 11 or more to 19 or less carbon atoms, such as for example at least one of stearic acid, palmitic acid, myristic acid, and lauric acid, a derivative belonging to those aliphatic acids, a cationic surfactant, an anionic surfactant, a nonionic surfactant, a amphipathic molecule having a phospholic group and a lipophilic group such as phospholipids, and the like. In addition, in one version, when an aromatic hydrocarbon having a functional group is used as each hydrophobic group of the ligand molecule-immobilized polymer, a functional group or material that binds to or otherwise interacts with the aromatic hydrocarbon can be used as the material having charge and hydrophobicity.

The size of the core particle 5 may be such that the diameter of the particle is from 10 nm to 10 μm. In one version, any material may be used in any layer of the core particle 5 except the outermost layer when the particle is formed of multiple layers, as long as the particle can be formed; for example, at least one of a magnetic substance, a fluorescent substance, an electrochemically active substance, a heavy metal substance, or a metal semiconductor substance can be used in any layer except the outermost layer. Examples of the magnetic substance can include, but are not limited to, iron oxide, chromium oxide, cobalt, and ferrite. Examples of the fluorescent substance can include, but are not limited to, fluoroscein, a cyanine-based dye, and a rare earth metal complex. Examples of the electrochemically active substance can include, but are not limited to, heavy metal complex substances such as an iron complex, a cobalt complex, and a nickel complex. Examples of the heavy metal substance can include, but are not limited to, nano metal particles each formed of, for example, gold, silver, or platinum. Examples of the metal semiconductor substance can include, but are not limited to, quantum dot materials such as CdSe fine particles.

In one version, the ligand molecule-immobilized particle according to the second embodiment of the present invention may be obtained by binding the ligand molecule-immobilized polymer to the core particle. Accordingly, in one embodiment, the present invention comprehends a method of producing the ligand molecule-immobilized particle, the method including: producing the above-described ligand molecule-immobilized polymer; and loading and mixing the ligand molecule-immobilized polymer into a solution having the core particle, the method being characterized in that the core particle has, on its surface, a charge different from the charge of the group having charge (e.g., $R_5$) of the ligand molecule-immobilized polymer, such as an opposing charge.

According to a third embodiment of the present invention, there is provided a method of separating a target substance in a sample that includes: (1) forming a composite A comprising the ligand molecule of the ligand molecule-immobilized particle described above, and the target substance captured (e.g., bound or held) by the ligand; and (2) separating the composite A.

Furthermore, in one version, as long as the target substance itself is a substance capable of transmitting a detectable signal, such as for example fluorescence, or the target substance has such a detectable substance, the target substance can be detected (when the method includes a step of detecting) after the separation of the target substance by the above steps (1) and (2). The detecting step in this case may be performed such that the detectable signal which the target substance can transmit is detected.

Figure 2:
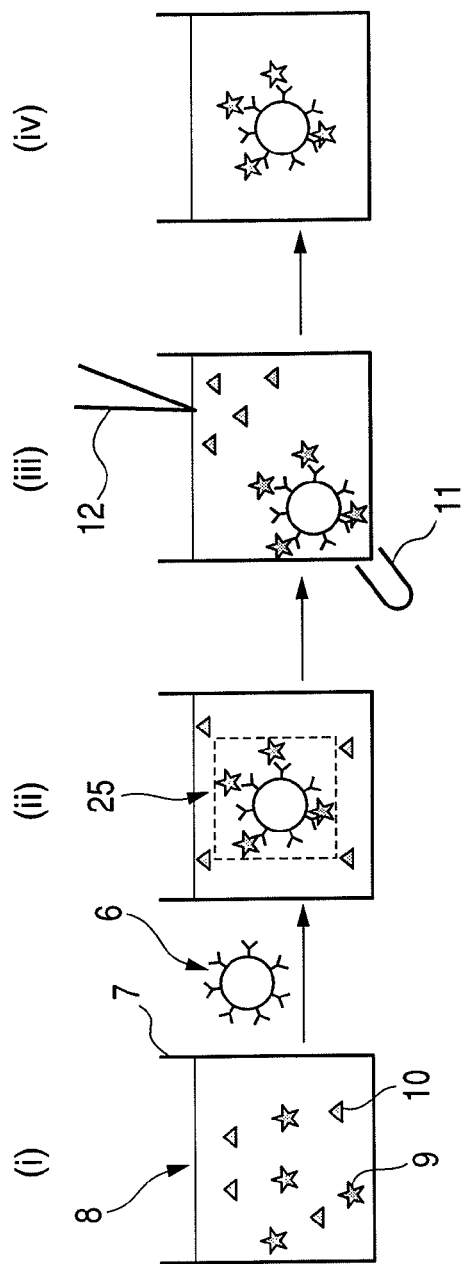
FIG. 2 illustrates schematic views (i), (ii), (iii) and (iv) for describing an embodiment of a B/F separation method involving the use of the ligand molecule-immobilized particle as a separation carrier.

FIGS. 2 and 5 are each a schematic view showing versions of the third embodiment of the present invention for separating the target substance in a sample.

First, FIG. 2 will be described.

As shown in (i) of the version shown in FIG. 2, the ligand molecule-immobilized particles 6 are added to a container 7 storing a sample 8 (e.g., a sample liquid) containing target substances 9 and contaminants 10, so that a composite A 25 of the target substances 9 and the ligand molecule-immobilized particle 6 is formed, as shown in (ii) of FIG. 2. Next, as shown in (iii) of FIG. 2, the remaining sample 8 may be taken up with a pipette 12 or the like while the formed composites A 25 are separately collected or accumulated with a magnet 11, for example at a specific portion of the container 7. As a result, the contaminants 10 and the composites A 25 present in the sample can be separated from each other, as shown in (iv) of FIG. 2. It should be noted that the method of separating the contaminants 10 and the composites A 25 as shown in (iii) of FIG. 2, is such that it allows the contaminants 10 and the composites A 25 to be separated from each other by an external action, but is not otherwise limited. For example, a centrifugation method as well as a magnetic separation method with a magnet can be suitably employed.

According to a fourth embodiment of the present invention, there is provided a method of detecting a target substance in a sample including:

(I) causing a first ligand molecule immobilized to a support to capture the target substance (in other words, forming a composite B formed of the first ligand molecule and the target substance);

(II) further causing a second ligand molecule, corresponding to the ligand molecule of the above-described ligand molecule-immobilized particle has to capture the same target substance which the first ligand molecule has captured (in other words, forming a composite C of a second ligand, which is the ligand molecule of the ligand molecule-immobilized particle, and the composite B, wherein the target substance is also captured by the second ligand); and (III) detecting the target substance captured by the first and second ligand molecules (in other words, detecting the target substance contained in the composite C).

Description of this embodiment will be given in greater detail with reference to FIGS. 3 to 5.

It should be noted that the ligand molecule-immobilized polymer is present between a second ligand molecule 15 and the particle 6, though the ligand molecule-immobilized polymer is omitted for purposes of clarity in the depictions in each one of FIGS. 3 to 5.

According to one version, in step (I), a sample containing the target substance 9 and the contaminants 10 is brought into contact with first ligand molecules 14 that are immobilized to the surface of a substrate 13 acting as a support, as shown in each of FIGS. 3 and 4. As a result, as shown in each of (B) of FIG. 3 and (b) of FIG. 4, the target substance 9 is specifically recognized and captured by one of the first ligand molecules 14, whereby the composite B is formed.

In the step (II) of this version, as shown in each of (C) of FIG. 3 and (d) of FIG. 4, one of the second ligand molecules 15, which is the ligand of the above-described ligand molecule-immobilized particle 6, is further caused to capture the target substance 9 that has been captured by one of the first ligand molecules 14 immobilized to the surface of the substrate 13. It should be noted that each of the first ligand molecules 14 may also optionally not be immobilized to the substrate, and may also optionally have a labeling material 17 as shown in (ii') of FIG. 5. In addition, in one version, the first ligand molecule 14 and the second ligand molecule 15 may recognize and capture different portions or regions of the target substance 9. In view of the foregoing, in one version, a secondary antibody can be suitably used as each of the second ligand molecules. In addition, as described above, the order in which the steps (I) and (II) are performed is not particularly limited, and is not limited to the particular sequence described above or shown in the figures, as long as the composite C 26 obtained by sandwiching the target substance 9 between the first ligand molecule 14 and the ligand molecule-immobilized particle 6 is formed. It should be noted that, in version of step (II), as shown in each of (b) of FIG. 4 and (c) of FIG. 4, the composite C can be formed by: bringing one of the second ligand molecules of the ligand molecule-immobilized polymer 16 into contact with the target substance 9 captured by one of the first ligand molecules 14 immobilized to the surface of the substrate 13; and bringing the core particle 5 into contact with the ligand molecule-immobilized polymer 16 after the former contact. In other words, the core particle can be immobilized to the ligand molecule-immobilized polymer after causing one of the second ligand molecules that forms a part of the ligand molecule-immobilized polymer to capture the target substance contained in the composite B.

In one version, the above steps (I) and (II) can be performed simultaneously. For example, in FIG. 5, the first ligand molecule 14 that is immobilized to the labeling material 17, and the ligand molecule-immobilized particle 6, are simultaneously added to the sample 8 stored in the container 7. The simultaneous addition in this version may allow for shortening of the reaction time. Alternatively, the following procedure can also be adopted: the ligand molecule-immobilized particle 6 having the second ligand molecules and the target substance 9 may be caused to react with each other in advance, and a first composite comprising the reacted ligand molecule-immobilized particle 6 and the target substance 9 may be caused to react with the first ligand molecule 14.

It should be noted that, for example as shown in (iii') of FIG. 5, a washing step of washing the formed composites C 26, such as by washing in a state where the composites are collected with the magnet 11 at a specific portion, can be performed between the steps (I) and (II) or after the step (II). When the washing step is performed, an unreacted target substance or the ligand molecule-immobilized particle is removed, whereby an increase in signal-noise ratio may be achieved.

In one version, in the step (III), the target substance 9 captured by the first ligand molecule 14 and the second ligand molecule 15 shown in each of (C) of FIG. 3 and (d) of FIG. 4 is detected. For example, as shown in each of (C) of FIG. 3 and (d) of FIG. 4, the target substance 9 may be detected by the following method: in the case where the substrate 13 has a detecting portion, the presence or absence, or number, of the target substances 9 captured by the first ligand molecules 14 immobilized to the surface of the substrate 13 and the second ligand molecules 15 of the ligand molecule-immobilized particles, may be detected directly or indirectly by the detecting portion. In another version, for example as shown in (iv') of FIG. 5, the target substances 9 may be detected by using the labeling materials 17 bound to the second ligand molecules in a state where the composites C 26 are present in a solution. In yet another version, such procedure as shown in (vi') of FIG. 5 may be adopted: the composite C 26 present in a solution is taken out of the solution, and is immobilized to the surface of a detecting substrate 18 before being detected. Here, the phrase "detected directly" means that at least one of the core particle 5, the ligand molecule-immobilized particle 6, and the labeling material 17 immobilized onto the substrate is detected. In addition, the phrase "detected indirectly" means that at least one of the core particle 5, the ligand molecule-immobilized particle 6, and the labeling material 17 is detected at a position distant from the substrate.

It should be noted that, in one version, the composites C 26 may be immobilized onto the surface of the detecting substrate 18 by any method that allows the particles to be specifically immobilized thereto. For example, in a version where a magnetic substance is used in each particle, the composites can be immobilized to the surface of the detecting substrate with a magnetic force. In addition, since the ligand molecule-immobilized particles each have charge, in one version the composites C may also be immobilized to the surface of the detecting substrate with an electrostatic interaction, for example by applying a voltage to the detecting substrate to polarize the substrate. Finally, the composites C immobilized to the surface of the detecting substrate may be detected directly or indirectly, whereby the target substances may be detected.

According to one aspect of the invention, the presence or absence, or number, of the immobilized composites C may be detected by any method as long as the presence or absence, or concentration, of the target substances in a sample can be detected by the method. For example, in a version where a magnetic substance is used in each particle, a mode involving the utilization of a magnetic field effect can be adopted; specifically, one or more of a magnetoresistance effect device, a Hall effect device, a magnetic impedance device, and a superconducting quantum interference device can be used as the substrate. In addition, in a version where a fluorescent substance is used in each particle, a mode involving the utilization of photo-detection can be adopted; specifically, at least one of a light emission, fluorescence, or phosphorescence measurement method involving the use of a plate reader can be employed. In addition, in a version where an electrochemically active substance is used in each particle, a mode involving the utilization of electrochemical detection can be adopted; specifically, a measurement method involving the use of an electrode in the substrate such as at least one of cyclic voltammetry, pulse voltammetry, amperometry, or coulometry can be employed. In addition, in another version, a mode according to which the number, or the molecular weight, of each of the particles is directly measured can be adopted; specifically, a method of counting the number of particles by at least one of SEM measurement or TEM measurement, or a method of measuring the molecular weight of each particle by MS measurement, can be employed.

It should be noted that in one embodiment, a target substance-detecting kit can be obtained by using, for example, the above materials, the particle, and the substrate.

For example, in one version there is provided a kit characterized by including:

(1-1) the detecting substrate to which the first ligand molecules are immobilized; and (1-2) the ligand molecule-immobilized particles having the second ligand molecules, (2-1) the detecting substrate to which the first ligand molecules are immobilized; (2-2) the ligand molecule-immobilized polymer; and (2-3) the core particles, or (3-1) the ligand molecule-immobilized particles having the first ligand molecules; (3-2) the labeling materials having the second ligand molecules; and (3-3) the detecting substrate.

In one embodiment of the detecting kit, a sample containing a target substance is introduced to the surface of the ligand molecule-immobilized detecting substrate and the ligand molecule-immobilized particles described in the above sections (1-1), (2-1), and (3-1), whereby the ligand molecule-immobilized particles, the core particles, and the labeling materials described in the above sections (1-2), (2-3), and (3-2) are immobilized onto the detecting substrate. Then, the presence or absence, and number of the ligand molecule-immobilized particles, the core particles, and the labeling materials may be detected, whereby at least one of the presence or absence, or concentration, of the target substance in the sample can be detected.

In one embodiment, the detecting kit can detect the presence or absence, and also the concentration of the target substance in the sample by directly or indirectly detecting at least one of the ligand molecule-immobilized particles, the core particles, and the labeling materials.

It should be noted that a ligand molecule is described with the term "first" or "second" in order that it can be determined which of the materials such as the ligand molecule-immobilized particle, the ligand molecule-immobilized polymer, the labeling material, and the detecting substrate, has the ligand molecule, in the case of a method involving the use of two kinds of ligand molecules such as a sandwich method. In addition, in one version a first ligand molecule and a second ligand molecule that are capable of capturing different regions of a target substance may be used in the sandwich method in ordinary cases. For example, in the case of a detecting kit having a "detecting substrate to which the first ligand molecule is immobilized" and a "ligand molecule-immobilized particle according to the present invention having the second ligand molecule", the first ligand molecule may be a ligand molecule which the detecting substrate has, and the second ligand molecule may be a ligand molecule which the ligand molecule-immobilized particle has.

EXAMPLE 1

This example relates to a production example of a ligand molecule-immobilized polymer and a production example of a ligand molecule-immobilized particle in the case where an antibody is used as a ligand molecule.

<1-1. Production of Ligand Molecule-Immobilized Polymer>

Figure 7:
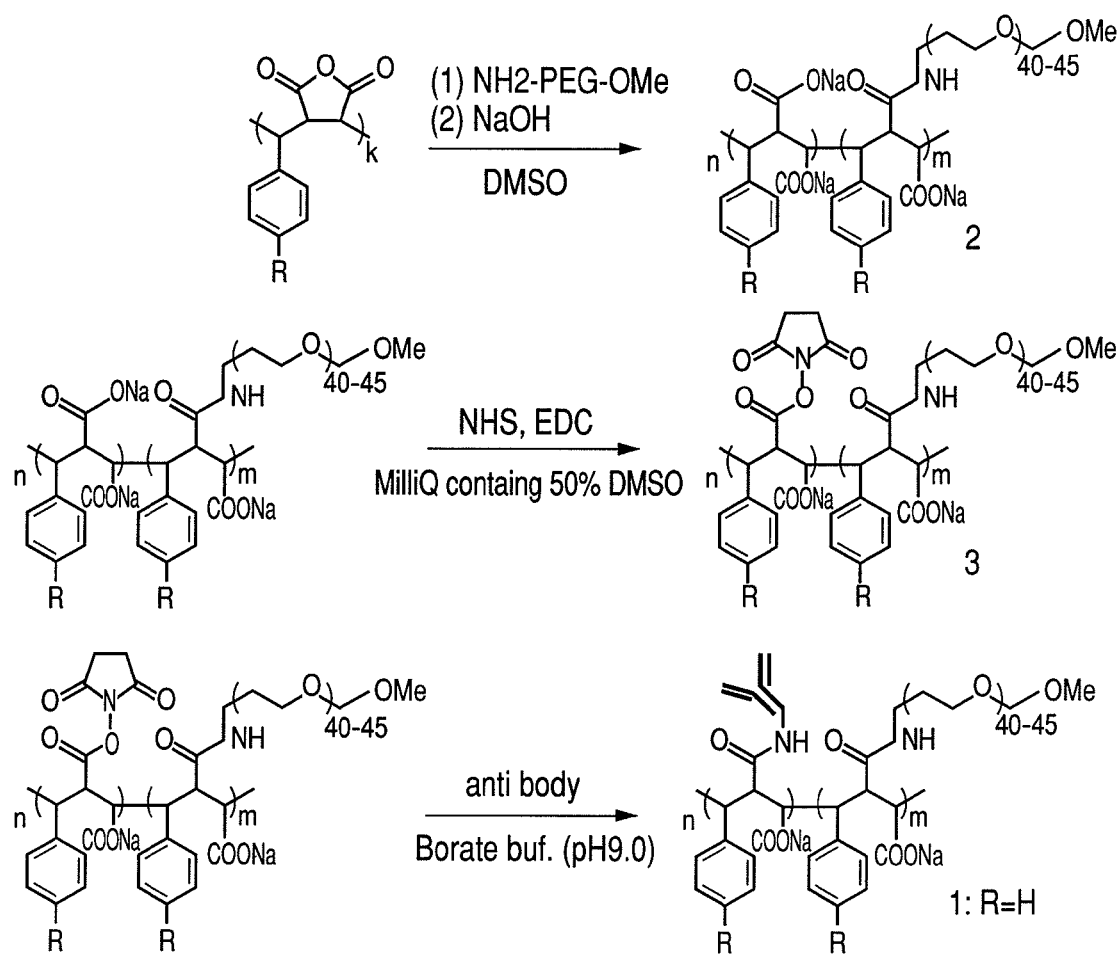
FIG. 7 is a view of an embodiment of a synthesis scheme for the ligand molecule-immobilized polymer.

A ligand molecule-immobilized polymer (hereinafter referred to as "antibody-immobilized polymer 1") was produced by using an antibody as a ligand molecule according to a scheme shown in FIG. 7.

(Synthesis of Compound 2)

50 mg of a styrene-alt-maleic anhydride copolymer (molecular weight ~360,000, manufactured by SIGMA-ALDRICH Corp.) and 0.2 mg of aminated methoxy polyethylene glycol (MEPA) (average molecular weight 2,000) (manufactured by NOF CORPORATION) were added to 500 μL of dimethyl sulfoxide (manufactured by Kishida Chemical Co., Ltd.), and the mixture was subjected to a reaction at room temperature all day long. After the reaction, the solution was applied to a Microcon YM-100 (manufactured by Millipore) so as to be centrifuged at 120×100 rpm for 10 minutes, whereby unreacted MEPA was removed. The solution obtained on the upper portion of the filter was recovered, and was dialyzed all day long. After the dialysis, the solution was freeze-dried, whereby a compound 2 was obtained. The compound 2 was identified by FT IR measurement and $^1$H NMR measurement.

(Synthesis of Compound 3)

35 mg of the resultant compound 2 were dissolved in 500 μL of a 0.05 M borate buffer (pH 9.0) containing 50% DMSO. After that, 5 mg of N-hydroxysuccinimide (manufactured by Tokyo Chemical Industry Co., Ltd.) were added to and completely dissolved in the solution. 5 mg of water soluble carbodiimide (WSCI) (manufactured by SIGMA-ALDRICH Corp.) were gradually added to the solution, and the mixture was stirred at room temperature for 3 hours. After the 3 hours, the reaction solution was applied to an NAP10 column (manufactured by GE Healthcare), and a target-derived component was purified with Milli Q water. The fractionated solution was freeze-dried, whereby a compound 3 was obtained. The compound 3 was identified by FT IR measurement and $^1$H NMR measurement.

(Synthesis of Compound 1 and Antibody-Immobilized Polymer 1)

Figure 8:
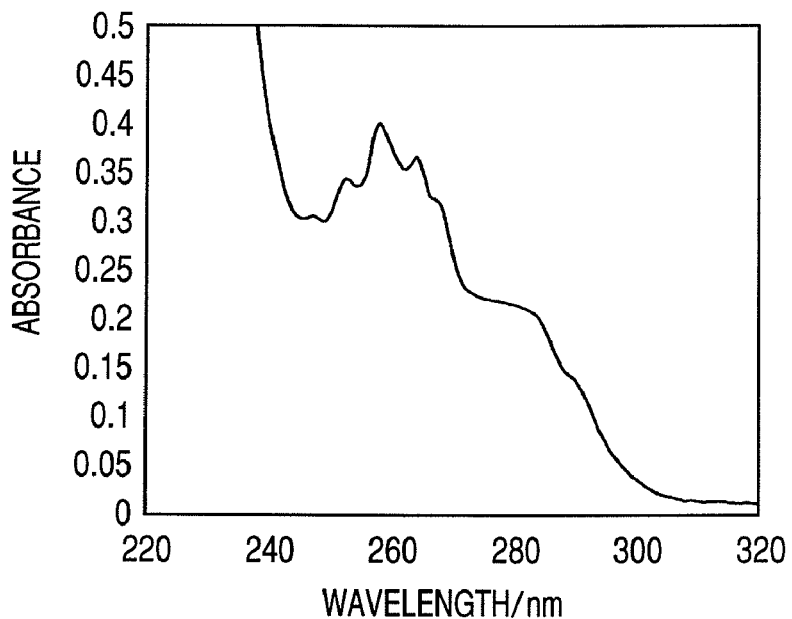
FIG. 8 is a view of the UV vis spectrum measurement of an embodiment of the ligand molecule-immobilized polymer.

10 mg of the resultant compound 3 were dissolved in 500 μL of a 0.05 M borate buffer (pH 9.0). After that, 1 mg of the antibody was added to the solution, and the mixture was subjected to a reaction at room temperature for 3 hours. After the reaction, the reaction solution was applied to a Microcon YM-100 so as to be centrifuged at 120×100 rpm for 10 minutes. Then, the solution obtained on the upper portion of the filter was recovered. A target-derived component was fractionated from the resultant solution with a gel filtration column chromatograph (AKTA, manufactured by GE Healthcare). The resultant solution was concentrated with the Microcon YM-100 again, whereby a compound 1 as a target was obtained. The compound 1 was identified by FT IR measurement, MALDI TOF MS measurement, and UV vis spectrum measurement. FIG. 8 shows the obtained result of the UV vis spectrum measurement. The obtained compound was judged to be the target from the result of the UV vis spectrum measurement because a styrene-derived absorption (λ=260 nm) and an antibody-derived absorption (λ=280 nm) were obtained. In addition, the amount of the antibody introduced into one polymer was calculated from the absorbances of the absorptions. As a result, it was found that one antibody was introduced into about one polymer.

<1-2. Production of Ligand Molecule-Immobilized Particles>

Ligand molecule-immobilized particles (hereinafter referred to as "antibody-immobilized particles") were produced by using the resultant antibody-immobilized polymer 1. Fluoroscein-encapsulating fluorescent particles (manufactured by Invitrogen Corporation) each having a diameter of 200 nm and an aminated surface, and ferrite-encapsulating magnetic particles (manufactured by ademtech) each having a diameter of 200 nm and an aminated surface were used as core particles. First, the particles were washed in advance with a phosphate buffer (pH 7.0) to be used. After the washing, the buffer containing the particles at a concentration of 1 mg/mL was mixed with 0.001, 0.01, 0.05, 0.1, 0.5, 1 mg of the antibody-immobilized polymer (10, 100, 500, 1,000, 5,000, or 10,000 antibody-immobilized polymers were added to one particle). Then, the particles and the polymer were caused to react with each other in the phosphate buffer at room temperature for 1 hour. After the reaction, the solution was irradiated with an ultrasonic wave for about 30 seconds, and was then centrifuged with a centrifuge at a predetermined number of revolutions for a predetermined time period. After the centrifugation, the supernatant solution was removed, and 500 μL of a phosphate buffer were added to the supernatant solution; the foregoing operation was repeated about four times, whereby the unreacted antibody-immobilized polymer was removed. After the purification, the result was stored in a solution containing a 1×PBS buffer (pH 7.0), a 1% BSA solution, and 0.05% TWEEN. The antibody-immobilized particles as targets were obtained by the above operations.

<1-3. Evaluation of Produced Antibody-Immobilized Particles for Dispersibility>

The produced antibody-immobilized particles were evaluated for their properties of dispersibility. The antibody-immobilized particles were evaluated for dispersibility by employing a dynamic light scattering measurement method. A 1-μg/mL solution of each of six kinds of antibody-immobilized particles (six kinds of particles obtained by adding 10, 100, 500, 1,000, 5,000, or 10,000 antibody-immobilized polymers to one particle) produced in the above section 1-2 was prepared. The solution was subjected to measurement with a dynamic light scattering photometer (OTSUKA ELECTRONICS CO., LTD.) so that the average particle diameter and grain size distribution of the antibody-immobilized particles were analyzed. Then, the particles were evaluated for dispersibility. For comparison, a 1-μg/mL solution of antibody-immobilized particles produced by a physical immobilization method as a conventional method was prepared, and the solution was subjected to measurement with the dynamic light scattering photometer so that the average particle diameter of the antibody-immobilized particles was determined.

Figure 9:
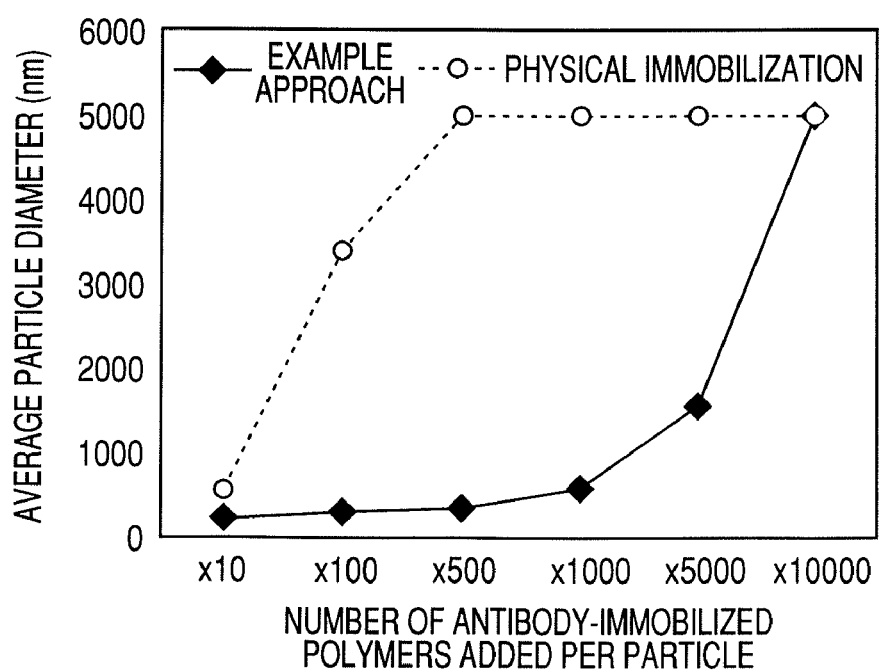
FIG. 9 is a view showing an example of a comparison between the average particle diameters of respective particles.

FIG. 9 shows a plot of the average particle diameters determined for the respective particles. The term "example approach" shown in FIG. 9 refers to particles produced by adding 10, 100, 500, 1,000, or 5,000 antibody-immobilized polymers to one particle while the term "physical immobilization" shown in the figure refers to particles each produced by: adding only 10, 100, 500, 1,000, or 5,000 antibodies to one particle; and immobilizing the antibodies to the surface of the particle by, for example, either a hydrophobic interaction or an electrostatic interaction. The results shown in FIG. 9 showed that the particles produced by the approach of the present example had a smaller average particle diameter than that of the particles produced by the physical immobilization, and were excellent in dispersibility. This is because, upon immobilization of the antibody-immobilized polymer of the present invention to each particle, a hydrophilic portion (PEG) in the polymer is positioned outside the surface of the particle, whereby the aggregation of the particles is prevented. On the other hand, in the case of the physical immobilization, charge on the surface of each particle is neutralized upon immobilization of the antibody, with the result that the aggregation of the particles is promoted, and the average particle diameter increases.

<1-4. Calculation of Number of Immobilized Antibodies on Surface of Produced Antibody-Immobilized Particle>

The number of immobilized antibodies on the surface of each antibody-immobilized particle was calculated as described below. The amount of the unreacted antibody-immobilized polymer obtained by the purification by centrifugation in the operations of the above section 1-2 was determined. The recovered unreacted antibody-immobilized polymer was mounted on a 6-μL microwell plate (manufactured by PerkinElmer, Inc.), and 200 μL of a Bradford indicator (manufactured by COSMOBIOS Co., Ltd.) were added to the polymer. 5 minutes after that, the plate was set in a fluorescent plate reader (manufactured by PerkinElmer, Inc.), and the absorbance of the polymer for light having a wavelength of 595 nm was measured. The amount of the unreacted antibody-immobilized polymer was determined from the resultant absorbance. The number of antibodies immobilized to the surface of each particle was determined from the resultant amount of the unreacted antibody-immobilized polymer. For comparison, the number of antibodies immobilized to the surface of each of antibody-immobilized particles produced by physical immobilization and chemical immobilization as conventional methods was determined by the same operations as those described above.

Figure 10:
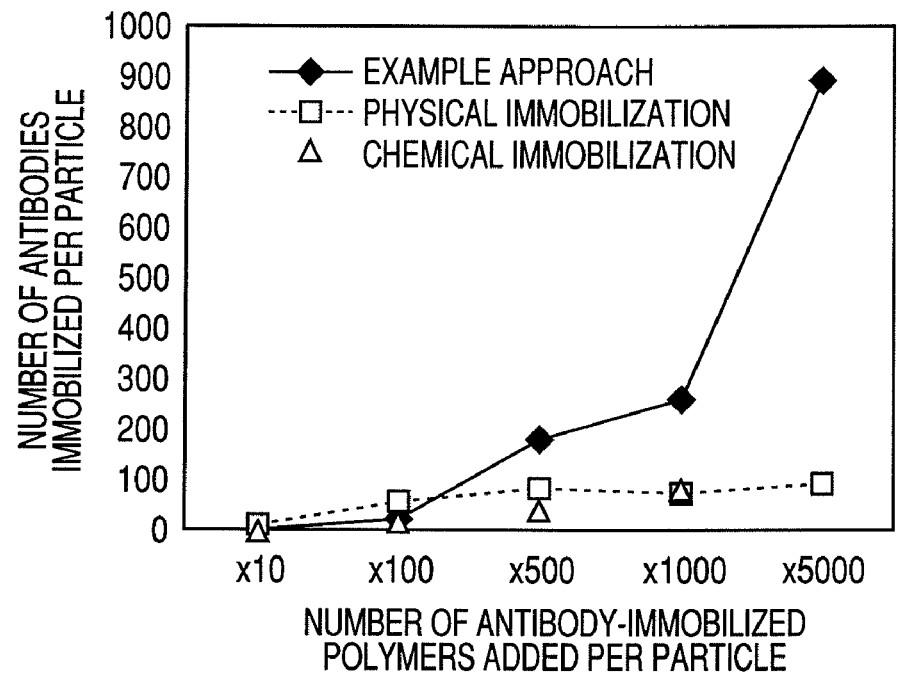
FIG. 10 is a view showing an example of a comparison among the numbers of immobilized antibodies of respective particles.

FIG. 10 shows a plot of the number of immobilized antibodies per one particle determined for the respective particles. The terms "example approach" and "physical immobilization" shown in FIG. 10 refer to the same production methods as those described in the above section 1-3, while the term "chemical immobilization" in the figure refers to particles each produced by: adding only 10, 100, 500, 1,000, or 5,000 antibodies to one particle; and immobilizing the antibodies onto the particle through amide bonds. The results shown in FIG. 10 showed that the particles produced by adding 500, 1,000, or 5,000 antibody-immobilized polymers to one particle showed a higher efficiency with which the antibodies were immobilized than those in the case of the particles produced by the physical immobilization and the chemical immobilization, and hence the immobilization of a large number of antibodies was attained.

<1-5. Evaluation of Each of Produced Antibody-Immobilized Particles for Affinity>

Each of the produced antibody-immobilized particles was evaluated for affinity for a target substance. The evaluation was performed with antibody-immobilized fluorescent particles by a sandwich immunoassay using a microwell plate shown in FIG. 6 on the basis of an obtained fluorescence intensity. Hereinafter, an experimental procedure for the sandwich immunoassay will be described. A 96-well microwell plate 19 (manufactured by PerkinElmer, Inc.) was prepared, the surface of which was made of polystyrene, and 100 μL of a solution of an anti-human chorionic Gonadotropin antibody (manufactured by Medix Biochemica) as a first ligand molecule at a concentration of 10 μg/mL was charged into each well 20. Then, the plate was left at rest all day long at 4° C., whereby the antibody was immobilized onto the plate. After the immobilization, the plate was washed with 250-μL portions of a phosphate buffer (pH 7.0) three times. After that, 200 μL of a 1% skim milk solution was charged into each well, and the plate was left at rest for 2 hours at room temperature, whereby the mixture in each well was blocked with a blocking agent 21. After the 2 hours, the plate was washed with 250-μL portions of a phosphate buffer (pH 7.0) three times. After that, 100 μL of a solution of human chorionic Gonadotropin (manufactured by ROHTO Pharmaceutical Co., Ltd.) at a concentration of 1 μg/mL was charged into each well, and the plate was left at rest for 2 hours at room temperature, whereby the mixture in each well was subjected to a reaction. After the 2 hours, the plate was washed with 250-μL portions of a phosphate buffer (pH 7.0) three times. After that, 100 μL of a solution of the produced antibody-immobilized fluorescent particles at a concentration of $2 \times 10^{10}$ particles/mL was charged into each well, and the mixture in each well was subjected to a reaction by being stirred for 1 hour or longer at room temperature. After a lapse of the 1 hour or longer, the plate was washed with 250-μL portions of a phosphate buffer (pH 7.0) three times, and 100 µL of a phosphate buffer was charged into each well. The plate was set in a fluorescent plate reader as a detecting apparatus 22, and each well was irradiated with light having a wavelength of 485 nm at a fluorescence energy of 10,000 J for an irradiation time of 1 second, whereby the fluorescence intensity of each particle for light having a wavelength of 535 nm was obtained. Each particle can be evaluated for affinity on the basis of the resultant fluorescence intensity because the fluorescence intensity corresponds to the amount of particles reacting with the target substance.

Figure 11:
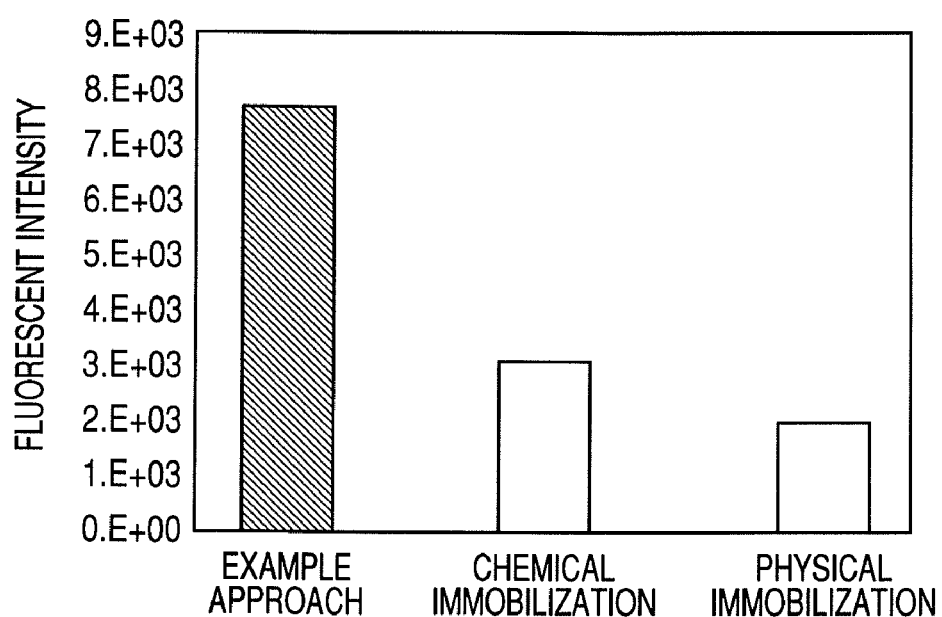
FIG. 11 is a view showing an example of a comparison among the fluorescence intensities of respective particles when the concentration of an antigen (target substance) is 1 µg/mL.

For comparison, the fluorescence intensity of each of the antibody-immobilized particles produced by the physical immobilization and the chemical immobilization as conventional methods was determined by the same operations as those described above. FIG. 11 shows the fluorescence intensities of respective particles produced by adding 1,000 antibody-immobilized polymers to one particle when the concentration of an antigen (target substance) is 1 µg/mL. Comparison among the resultant fluorescence intensities showed that the particles produced by the approach of the present example each showed a higher affinity than those of the other particles.

Figure 12:
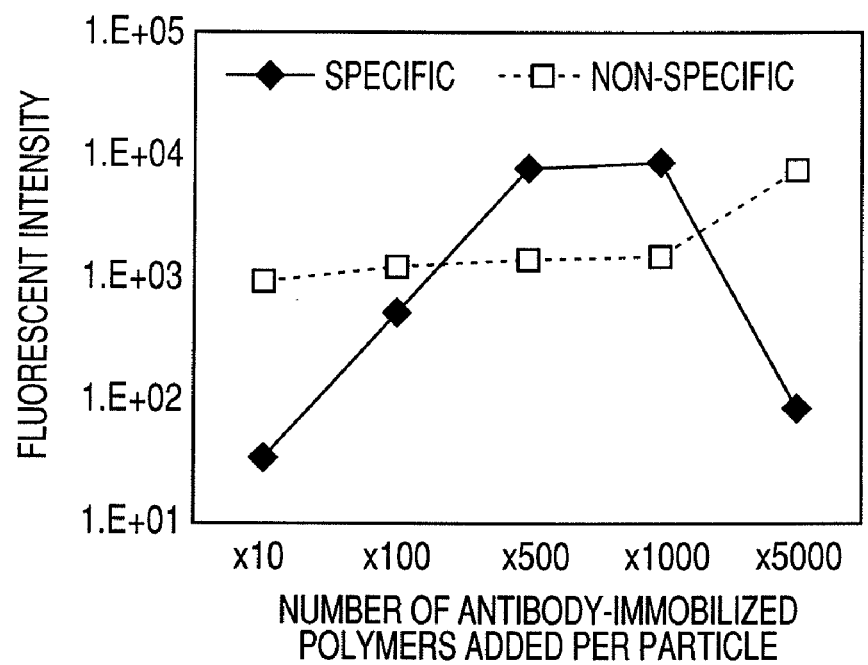
FIG. 12 is a view showing an example of a comparison among the fluorescence intensities of respective particles when the concentration of an antigen (target substance) is 1 µg/mL.

Next, the affinities of the five kinds of antibody-immobilized particles (five kinds of particles produced by adding 10, 100, 500, 1,000, or 5,000 antibody-immobilized polymers to one particle) produced in the above section 1-2 were compared on the basis of the fluorescence intensities of the particles obtained by the same experiment as that described above. FIG. 12 shows the fluorescence intensities of the respective particles when the concentration of the antigen (target substance) is 1 µg/mL. The resultant fluorescence intensities showed that the particles each produced by adding 1,000 antibody-immobilized polymers to one core particle each showed the highest affinity out of the five kinds of particles.

EXAMPLE 2

This example is a B/F separation example when the antibody-immobilized particles are each used as a separation carrier.

<2-1. B/F Separation of Target Substance by Centrifugation Method>

The antibody-immobilized particles produced in Example 1 are added to a sample containing human chorionic Gonadotropin as a target substance so as to have a concentration of 1 mg/mL. The solution is incubated at room temperature for 15 minutes or longer. After the incubation, the solution is subjected to a centrifuge so that the antibody-immobilized particles are precipitated. After the supernatant has been removed, the precipitated antibody-immobilized particles are dispersed by stirring; the operation is repeated three or more times. As a result of the foregoing operations, only human chorionic Gonadotropin in the sample is captured to each of the antibody-immobilized particles, and a contaminant in the sample is removed.

To determine whether human chorionic Gonadotropin is captured to each of the resultant antibody-immobilized particles, the particles are each evaluated for B/F separation ability by the sandwich immunoassay using a microwell plate described in Example 1. The operations are as described below. 100 µL of a solution of an anti-human chorionic Gonadotropin antibody as a first ligand molecule at a concentration of 10 µg/mL is charged into the microwell plate, and the plate is left at rest all day long at 4° C., whereby the antibody is immobilized onto the plate. After the immobilization, the plate is washed with 250-µL portions of a phosphate buffer (pH 7.0) three times. After that, 200 µL of a 1% skim milk solution is charged into each well, and the plate is left at rest for 2 hours at room temperature, whereby the plate is masked. After the 2 hours, the plate is washed with 250-µL portions of a phosphate buffer (pH 7.0) three times. After that, 100 µL of a solution of the antibody-immobilized particles obtained by the above operations is charged into each well, and the mixture in each well is subjected to a reaction by being stirred for 1 hour or longer at room temperature. After the reaction, the plate is washed with 250-µL portions of a phosphate buffer (pH 7.0) three times, and then 100 µL of a phosphate buffer are charged into each well. The plate is set in a fluorescent plate reader, and each well is irradiated with light having a wavelength of 485 nm at a fluorescence energy of 10,000 J for an irradiation time of 1 second, whereby the fluorescence intensity of each particle for light having a wavelength of 535 nm is obtained. The amount of human chorionic Gonadotropin captured onto the antibody-immobilized particles is estimated from the resultant fluorescence intensities, and the B/F separation abilities of the antibody-immobilized particles are compared and evaluated. Particles to be compared therewith that are described here are antibody-immobilized particles each having a diameter of 200 nm produced on the basis of the chemical immobilization method and the physical immobilization method as conventional methods.

<2-2. B/F Separation of Target Substance by Magnetic Handling>

Antibody-immobilized magnetic particles are produced by using the antibody-immobilized polymer obtained in the above section 1-1 of Example 1. Ferrite particle-encapsulating magnetic particles (manufactured by ademtech) each having a diameter of 200 nm and an aminated surface are used as particles. First, the magnetic particles are washed in advance with a buffer to be used. After the washing, 1 mg of a solution of the antibody-immobilized polymer is charged into the buffer containing the magnetic particles at a concentration of 1 mg/mL, and the particles and the polymer are caused to react with each other in the buffer at 25° C. for 1 hour or longer. After the reaction, the solution is irradiated with an ultrasonic wave for about 30 seconds, and then the antibody-immobilized magnetic particles and the unreacted antibody-immobilized polymer are separated from each other with a magnet so that the unreacted antibody is removed; the operation is repeated about four times. After the purification, the resultant is stored in a solution containing a 10 mM tris hydrochloride buffer (pH 7.0), a 1% BSA solution, and 0.05% TWEEN.

Hereinafter, B/F separation is performed by magnetic handling according to the method shown in FIGS. 2(i) to 2(iv). A solution containing α subunit-recognizing antibody-immobilized particles produced by the above operations at a concentration of 1 mg/mL and a sample liquid containing human chorionic Gonadotropin as a target substance are mixed, and the mixed solution is incubated at room temperature for 15 minutes or longer. After the incubation, a magnet is brought close to the mixed solution to separate the antibody-immobilized particles from the solution. After the supernatant has been removed in the state, the separated antibody-immobilized particles are dispersed by stirring; the operation is repeated three or more times. Only human chorionic Gonadotropin in the sample is captured to each of the antibody-immobilized particles by the above operations, whereby a contaminant in the sample is removed.

To determine whether human chorionic Gonadotropin is captured to each of the resultant antibody-immobilized particles, each of the antibody-immobilized particles is subjected to a sandwich reaction with an anti-human chorionic Gonadotropin antibody having a fluorescent dye, and the particles are each evaluated for B/F separation ability by using the fluorescence intensity of the fluorescent dye. The operations are as described below. An anti-human chorionic Gonadotropin antibody having fluoroscein is added to a solution of the resultant antibody-immobilized particles so as to have a final concentration of 10 μg/mL. Then, the mixed solution is stirred at room temperature for 15 minutes or longer. After the reaction, a magnet is brought close to the mixed solution to separate the antibody-immobilized particles from the solution. After the supernatant has been removed in the state, the separated antibody-immobilized particles are dispersed by stirring; the operation is repeated three or more times. After the purification, the solution is irradiated with light having a wavelength of 485 nm from a fluorophotometer (manufactured by Hitachi, Ltd.) or a fluorescent plate reader so that light having a wavelength of 535 nm is detected. The amount of human chorionic Gonadotropin captured onto the antibody-immobilized particles is estimated from the resultant fluorescence intensity, and the B/F separation abilities of the antibody-immobilized particles are compared and evaluated. Particles to be compared therewith that are described herein are antibody-immobilized particles each having a diameter of 200 nm that are produced on the basis of the production methods described in Japanese Patent Application Laid-Open No. S59-135887.

EXAMPLE 3

This example relates to an example of the detection of a target substance by a sandwich immunoassay when the antibody-immobilized particles produced in Example 1 are each used as a labeling agent, and an example of the detection of the target substance by the sandwich immunoassay when the antibody-immobilized polymer produced in Example 1 is used as a labeling agent. In this example, human chorionic Gonadotropin as the target substance was detected with a fluorescent plate reader by using a microwell plate as a substrate and an anti-human chorionic Gonadotropin antibody as a first ligand molecule in order that the sandwich immunoassay might be performed.

<3-1. Sandwich Immunoassay Using Antibody-Immobilized Particle as Labeling Agent>

Figure 13:
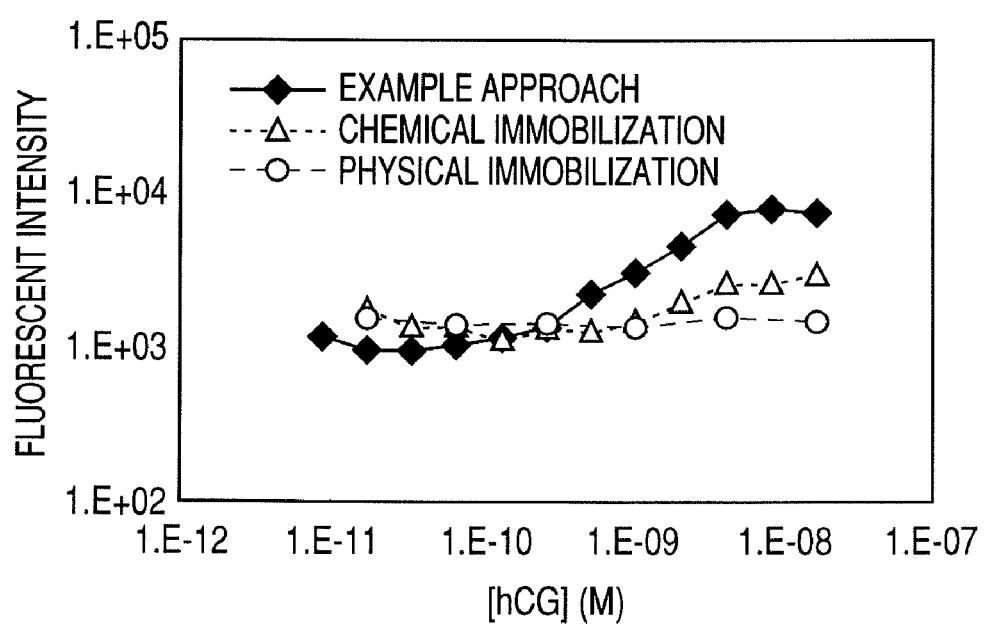
FIG. 13 is a view showing an example of the calibration curves of respective particles.

A 96-well microwell plate was prepared, the surface of which was made of polystyrene, and 100 μL of a solution of the anti-human chorionic Gonadotropin antibody as a first ligand molecule at a concentration of 10 μg/mL was charged into each well. Then, the plate was left at rest all day long at 4° C., whereby the antibody was immobilized onto the plate. After the immobilization, the plate was washed with 250-μL portions of a phosphate buffer (pH 7.0) three times. After that, 200 μL of a 1% skim milk solution was charged into each well, and the plate was left at rest for 2 hours at room temperature, whereby the plate was masked. After the 2 hours, the plate was washed with 250-μL portions of a phosphate buffer (pH 7.0) three times. After that, 100 μL of a solution of human chorionic Gonadotropin at a concentration of 1 ng/mL to 1 μg/mL was charged into each well, and the plate was left at rest for 2 hours at room temperature, whereby the mixture in each well was subjected to a reaction. After the 2 hours, the plate was washed with 250-μL portions of a phosphate buffer (pH 7.0) three times. After that, 100 μL of a solution of the antibody-immobilized fluorescent particles each having an α subunit-recognizing antibody produced in the above section 1-2 of Example 1 at a concentration of $2 \times 10^{10}$ particles/mL was charged into each well, and the mixture in each well was subjected to a reaction by being stirred for 1 hour or longer at room temperature. After a lapse of the 1 hour or longer, the plate was washed with 250-μL portions of a phosphate buffer (pH 7.0) three times, and 100 μL of a phosphate buffer was charged into each well. The plate was set in the fluorescent plate reader, and each well was irradiated with light having a wavelength of 485 nm at a fluorescence energy of 10,000 J for an irradiation time of 1 second, whereby the fluorescence intensity of each particle for light having a wavelength of 535 nm was obtained. A calibration curve was obtained by plotting the resultant fluorescence intensities versus the concentration of added human chorionic Gonadotropin. For comparison, the fluorescence intensities of antibody-immobilized particles produced by the physical immobilization and the chemical immobilization as conventional methods were determined by the same operations as those described above. FIG. 13 shows the resultant calibration curves. Comparison among the resultant calibration curves showed that the particles produced by the approach according to the present example each had a detection sensitivity one or more orders of magnitude higher than that of each of the other particles.

<3-2. Sandwich Immunoassay Using Antibody-Immobilized Polymer>

A 96-well microwell plate is prepared, the surface of which is made of polystyrene, and 100 μL of a solution of the anti-human chorionic Gonadotropin antibody as a first ligand molecule at a concentration of 10 μg/mL is charged into each well. Then, the plate is left at rest all day long at 4° C., whereby the antibody is immobilized onto the plate. After the immobilization, the plate is washed with 250-μL portions of a phosphate buffer (pH 7.0) three times. After that, 200 μL of a 1% skim milk solution is charged into each well, and the plate is left at rest for 2 hours at room temperature, whereby the plate is masked. After the 2 hours, the plate is washed with 250-μL portions of a phosphate buffer (pH 7.0) three times. After that, 100 μL of a solution of human chorionic Gonadotropin at a concentration of 1 ng/mL to 1 μg/mL is charged into each well, and the plate is left at rest for 2 hours at room temperature, whereby the mixture in each well is subjected to a reaction. After the 2 hours, the plate is washed with 250-μL portions of a phosphate buffer (pH 7.0) three times. After that, 100 μL of a solution of the antibody-immobilized polymer having an α subunit-recognizing antibody produced in the above section 1-1 of Example 1 (1 μM) is charged into each well, and the mixture in each well is subjected to a reaction by being stirred for 1 hour or longer at room temperature. After a lapse of the 1 hour or longer, the plate is washed with 250-μL portions of a phosphate buffer (pH 7.0) three times, and 100 μL of a solution of fluorescent particles each having a diameter of 200 nm and an aminated surface at a concentration of $1 \times 10^{11}$ particles/mL is charged into each well, and the mixture in each well is subjected to a reaction by being stirred for 1 hour or longer at room temperature. After a lapse of the 1 hour or longer, the plate is washed with 250-μL portions of a phosphate buffer (pH 7.0) three times, and 100 μL of a phosphate buffer are charged into each well. The plate is set in the fluorescent plate reader (manufactured by PerkinElmer, Inc.), and each well is irradiated with light having a wavelength of 485 nm at a fluorescence energy of 10,000 J for an irradiation time of 1 second, whereby the fluorescence intensity of each particle for light having a wavelength of 535 nm is obtained. A calibration curve is obtained by plotting the resultant fluorescence intensities versus the concentration of added human chorionic Gonadotropin.

EXAMPLE 4

This example is an example of the detection of a target substance by a sandwich immunoassay when the antibody-immobilized particles produced in Example 1 are each used as a carrier. In this example, human chorionic Gonadotropin as the target substance is detected with a fluorescent plate reader by using a microwell plate as a detecting substrate and an anti-human chorionic Gonadotropin antibody having fluoroscein as a labeling material.

A solution of human chorionic Gonadotropin as the target substance is charged into a solution of the antibody-immobilized magnetic particles each having an α subunit-recognizing antibody produced in the above section 1-2 of Example 1 so as to have a final concentration of 1 ng/mL to 1 µg/mL. Further, the anti-human chorionic Gonadotropin antibody having fluoroscein is added to the solution so as to have a final concentration of 10 µg/mL. Then, the mixed solution is stirred at room temperature for 15 minutes or longer. After the reaction, a magnet is brought close to the mixed solution to separate the antibody-immobilized particles from the solution. After the supernatant has been removed in the state, the separated antibody-immobilized particles are dispersed by stirring; the operation is repeated three or more times. After the purification, the solution is irradiated with light having a wavelength of 485 nm from a fluorophotometer (manufactured by Hitachi, Ltd.) or the fluorescent plate reader so that light having a wavelength of 535 nm is detected. A calibration curve is obtained by plotting the resultant fluorescence intensities versus the concentration of added human chorionic Gonadotropin.

Accordingly, the above-described examples in accordance with aspects of the invention can provide ligand molecule-immobilized particles that have reduced, and even negligible, aggregation and have a large amount of ligand molecules immobilized to their surfaces, and also a ligand molecule-immobilized polymer that can be used in, for example, each of the ligand molecule-immobilized particles.

In addition, the use of the ligand molecule-immobilized particles according to the approach in the examples can realize high-sensitivity, high-accuracy detection of a target substance, and high-sensitivity, high-accuracy separation of the target substance.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2007-307486, filed Nov. 28, 2007 and 2008-122163, filed May 8, 2008, which are hereby incorporated by reference herein in their entirety.

What is claimed is:

1. A ligand molecule-immobilized particle, comprising:
a core particle, a surface of which has hydrophobicity and charge; and
a ligand molecule-immobilized polymer immobilized to the surface of the core particle, wherein:
the ligand molecule-immobilized polymer comprises a structure represented by the following general formula (1):

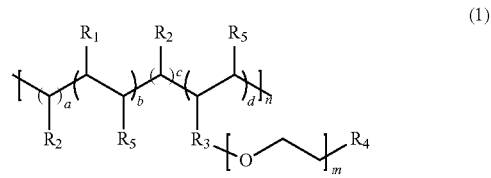

where $R_1$ represents a ligand molecule-containing group, $R_2$ represents a hydrophobic group, $R_3$ represents a spacer site, $R_4$ represents a hydrophilic group, $R_5$ represents a group having charge, a to d specify a composition ratio and each represent an integer of 1 or more, and n and m specify chain lengths and represent integers satisfying relationships of $1 \leq n(a+b+c+d) \leq 10{,}000$ and $1 \leq m \leq 350$,
a charge $Q_1$ of the group having charge in the ligand molecule-immobilized polymer, and a charge $Q_2$ on the surface of the core particle satisfy a relationship of $Q_1 \times Q_2 < 0$ in a sample liquid, and
the number of the ligand molecule-containing groups per particle is 200 or more to 900 or less.

2. A ligand molecule-immobilized particle according to claim 1, wherein the ligand molecule-containing group comprises an antibody.

3. A ligand molecule-immobilized particle according to claim 1, wherein the core particle comprises an aminated surface.

4. A ligand molecule-immobilized particle according to claim 1, wherein the structure represented by the general formula (1) comprises the following compound:

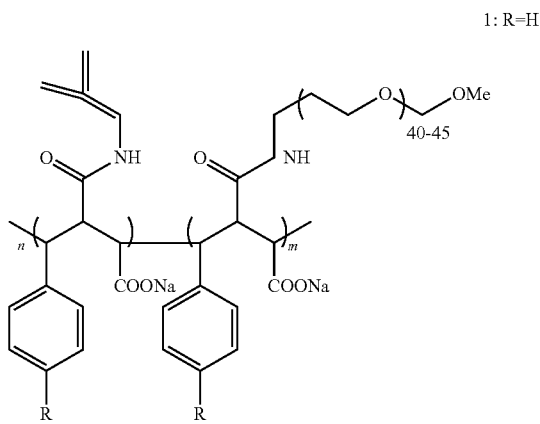

where the symbol

represents a ligand molecule.

* * * * *